(12) United States Patent
Cheong et al.

(10) Patent No.: US 8,546,544 B2
(45) Date of Patent: Oct. 1, 2013

(54) ANTIBODY SPECIFICALLY BINDING TO C-MET AND METHODS OF USE

(75) Inventors: Kwang-ho Cheong, Seongnam-si (KR); Sung-young Jeong, Yongin-si (KR); Sang-hyun Paek, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 249 days.

(21) Appl. No.: 12/807,191

(22) Filed: Aug. 30, 2010

(65) Prior Publication Data

US 2011/0129481 A1    Jun. 2, 2011

(30) Foreign Application Priority Data

Nov. 27, 2009 (KR) .................. 10-2009-0115927

(51) Int. Cl.
  *C07K 16/26* (2006.01)
  *C07K 16/00* (2006.01)
  *C12N 5/20* (2006.01)
  *C12N 15/00* (2006.01)
  *C12N 15/87* (2006.01)
  *C07H 21/04* (2006.01)

(52) U.S. Cl.
  USPC ............... 530/388.24; 530/388.1; 435/326; 435/320.1; 435/455; 536/23.53; 424/9.341

(58) Field of Classification Search
  None
  See application file for complete search history.

(56) References Cited

U.S. PATENT DOCUMENTS

| 5,686,292 | A | 11/1997 | Schwall et al. |
| 6,214,344 | B1 | 4/2001 | Schwall et al. |
| 7,556,804 | B2 | 7/2009 | Prat |
| 2006/0134104 | A1 | 6/2006 | Dennis et al. |
| 2009/0175860 | A1 | 7/2009 | Stover et al. |
| 2009/0285807 | A1 | 11/2009 | Comoglio et al. |

FOREIGN PATENT DOCUMENTS

| EP | 1997511 A1 | 12/2008 |
| EP | 2014681 A1 | 1/2009 |
| KR | 1020080113218 A | 12/2008 |
| KR | 1020090013745 A | 2/2009 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Schteingart et al. (Endocrine-Related Cancer 2005, 12:667-680).*

* cited by examiner

*Primary Examiner* — Sharon Wen
(74) *Attorney, Agent, or Firm* — Leydig, Voit & Mayer, Ltd.

(57) ABSTRACT

Antibodies specifically binding to c-Met protein, hybridoma cell lines, and compositions comprising the antibodies are disclosed herein. Methods of making and using the antibodies and compositions are also disclosed.

27 Claims, 4 Drawing Sheets
(3 of 4 Drawing Sheet(s) Filed in Color)

ANTIBODY SPECIFICALLY BINDING TO C-MET AND METHODS OF USE

CROSS-REFERENCE TO RELATED APPLICATIONS

This application claims the benefit of Korean Patent Application No. 10-2009-0115927, filed on Nov. 27, 2009, and all the benefits accruing therefrom under 35 U.S.C. §119, the disclosure of which is incorporated herein in its entirety by reference.

BACKGROUND

1. Field

The present disclosure relates to antibodies specifically binding to c-Met and kits for diagnosing cancer using the antibodies.

2. Description of the Related Art

Hepatocyte growth factor (HGF) is a mesenchyme-derived pleitrophic cytokine that binds the extracellular region of the tyrosine kinase receptor, c-Met, to induce mitogenesis, movement, morphogenesis, and angiogenesis in various normal cells and tumor cells. Regulation of the HGF/c-Met signaling pathway is implicated in various mechanisms related to cancer, such as tumor progression, metastasis, migration, invasion, and angiogenesis. In addition, c-Met amplification or mutation is thought to drive ligand-independent tumorogenesis. Thus, c-Met has recently emerged as a new target for anti-cancer therapy.

c-Met interacts with proteins in the ErbB family, such as ERBB1 (epidermal growth factor receptor (EGFR)), ERBB2 (HER2), or the like, in intracellular signal transduction. Representative anti-cancer drugs targeting EGFR (ERBB1), i.e., Erbitux or Tarceva, work by blocking signal transduction related to a cancer development. Herceptin, which is a well known breast cancer drug, targets ERBB2 (HER2) and works by blocking signal transduction necessary for cell proliferation. However, recent findings indicate that among patients resistant to the drugs described above, the anti-cancer drugs do not work due to overexpression of c-Met protein and activation of other types of signal transduction that lead to cell proliferation. Thus, many pharmaceutical firms are developing anti-cancer drugs to inhibit c-Met.

In addition, c-Met is over-expressed in various kinds of cancers. In particular, most cancer cases in which the probability that the patient will recover from the illness is negative are known to be related to over-expression of c-Met. Thus, antibodies specifically binding to c-Met may be used for measuring c-Met expression in a patient clinical sample, and may thereby provide information that helps doctors decide on therapeutic action in treating the cancer.

Therefore, there is a continuing need for development of antibodies that specifically bind to c-Met and kits for detecting cancer using the antibodies.

SUMMARY

Provided are antibodies specifically binding to c-Met protein or antigen binding fragments thereof.

In an embodiment, the antibody is produced from a hybridoma cell having Accession No. KCLRF-BP-00219.

In an embodiment, the antibody is produced from a hybridoma cell having Accession No. KCLRF-BP-00223.

In an embodiment, the isolated antibody or an antigen binding fragment thereof, includes a heavy chain variable region comprising at least one heavy chain complementarity determining region (CDR) amino acid sequence selected from the group consisting of SEQ ID NO: 1, SEQ ID NO: 2, and SEQ ID NO: 3; and a light chain variable region comprising at least one light chain CDR amino acid sequence selected from the group consisting of SEQ ID NO: 5, SEQ ID NO: 6, and SEQ ID NO: 7.

In an embodiment, the isolated antibody or the antigen binding fragment thereof includes a heavy chain variable region comprising at least one heavy chain complementarity determining region (CDR) amino acid sequence selected from the group consisting of SEQ ID NO: 9, SEQ ID NO: 10, and SEQ ID NO: 11; and a light chain variable region comprising at least one light chain CDR amino acid sequence selected from the group consisting of SEQ ID NO: 13, SEQ ID NO: 14, and SEQ ID NO: 15, or antigen binding fragments thereof.

Provided are polynucleotides that encode the heavy chain variable region or the light chain variable region of an antibody disclosed herein.

Provided are recombinant vectors including the polynucleotides disclosed herein, and host cells transformed with the recombinant vectors.

Provided are compositions including the antibodies or antigen-binding antibody fragments.

Methods of making and using the antibodies and compositions are also disclosed.

Additionally, hybridoma cell lines producing the antibodies are disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects, advantages, and features of this disclosure will become apparent and more readily appreciated from the following description of exemplary embodiments, taken in conjunction with the accompanying drawings in which:

FIG. 3C) for immunostaining, respectively, according to embodiments of the invention.

DETAILED DESCRIPTION

Figure 1:
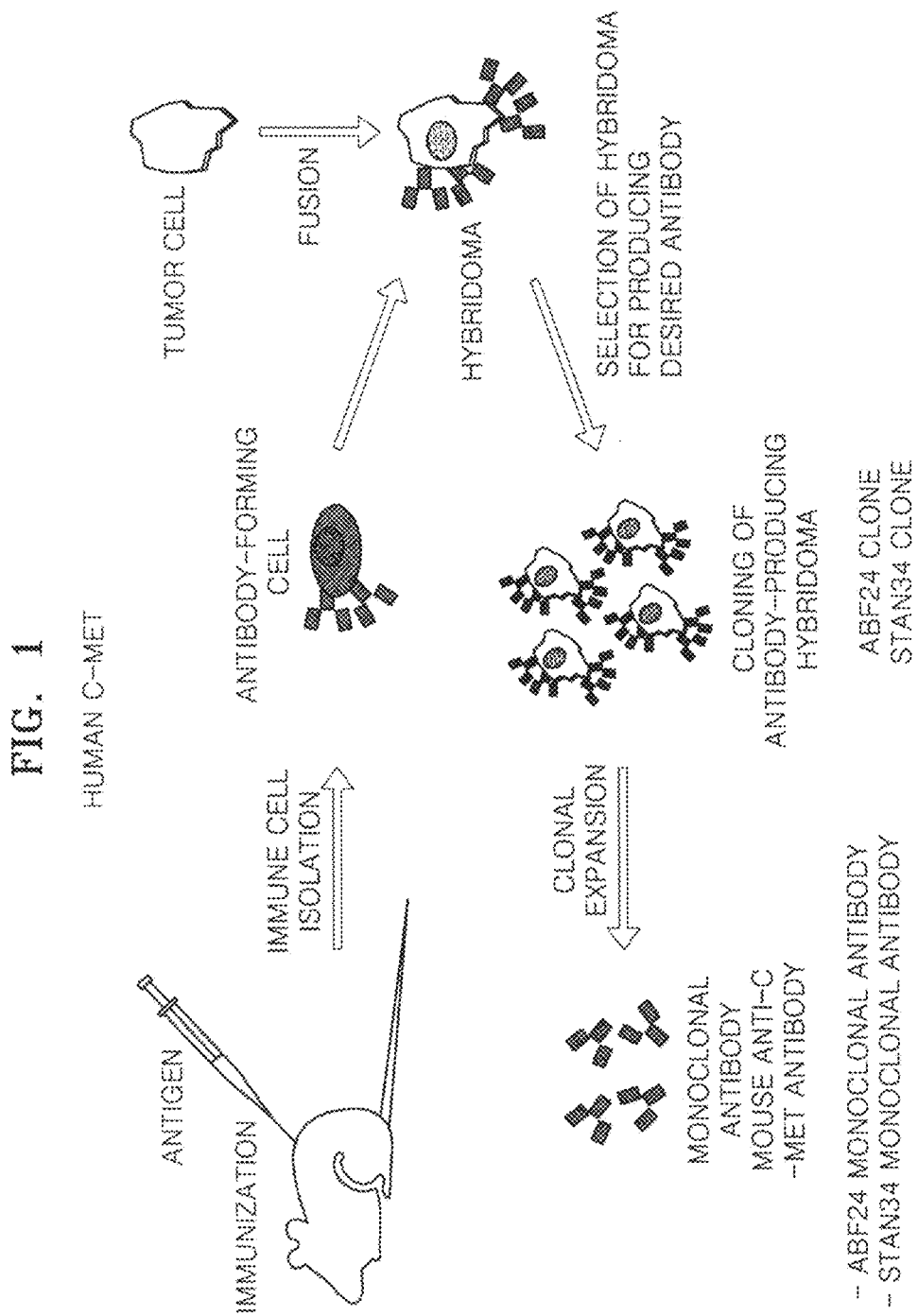
FIG. 1 is a schematic diagram illustrating a process of producing monoclonal antibodies AbF24 and Stan34, according to an embodiment of the invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

According to an embodiment of the invention, there is provided a monoclonal antibody that is produced by a hybridoma cell having an accession number of KCLRF-BP-00219, and specifically binds c-Met protein.

According to an embodiment of the invention, there is provided a monoclonal antibody that is produced by a hybridoma cell having an accession number of KCLRF-BP-00223, and specifically binds c-Met protein.

The term "c-Met" or "c-Met protein" refers to a receptor tyrosine kinase that specifically binds hepatocyte growth factor (HGF). The receptor tyrosine kinase c-Met participates in various mechanisms such as cancer development, metastasis, migration, invasion, and angiogenesis.

The term "specifically binding" or "specifically recognized" herein means that an antibody exhibits appreciable affinity for an antigen or a particular epitope and, preferably, does not exhibit significant crossreactivity. "Appreciable" binding affinity includes binding with an affinity of at least $10^6$ $M^{-1}$, specifically at least $10^7 M^{-1}$, more specifically at least $10^8 M^{-1}$, yet more specifically at least $10^9$ $M^{-1}$, or even yet more specifically at least $10^{10}$ $M^{-1}$. A binding affinity can also be indicated as a range of affinities, for example, $10^6 M^{-1}$ to $10^{10}$ $M^{-1}$, specifically $10^7 M^{-1}$ to $10^{10}$ $M^{-1}$, more specifically $10^8 M^{-1}$ to $10^{10}$ M. An antibody that "does not exhibit significant crossreactivity" is one that will not appreciably bind to an undesirable entity (e.g., an undesirable proteinaceous entity). An antibody specific for a particular epitope will, for example, not significantly crossreact with remote epitopes on the same protein or peptide. Specific binding can be determined according to any art-recognized means for determining such binding. In some embodiments, specific binding is determined according to Scatchard analysis and/or competitive binding assays.

A naturally occurring intact antibody, or immunoglobulin, includes four polypeptides: two full-length light chains and two full-length heavy chains, in which each light chain is linked to a heavy chain by disulfide bonds. Each heavy chain has a constant region and a variable region. Similarly, each light chain has a constant region and a variable region. There are five heavy chain classes (isotypes): gamma (γ), mu (μ), alpha (α), delta (δ), or epsilon (ε), and additionally several subclasses gamma 1 (γ1), gamma 2(γ2), gamma 3(γ3), gamma 4(γ4), alpha 1(α1), and alpha 2(α2). The light chain constant region can be either kappa (κ) or lambda (λ) type. The variable regions differ in sequence among antibodies and are used in the binding and specificity of a given antibody to its particular antigen.

The term "monoclonal antibody" used herein refers to all antibodies derived from a single cell clone. A monoclonal antibody has a binding specificity to a single antigen and affinity for only a specific epitope of the antigen.

A hybridoma cell may be prepared using any method known in the art. For example, a hybridoma cell may be prepared by immunizing an animal with the immunogen, c-Met protein; fusing antibody-producing cells, B cells, derived from the immunized animal with myeloma cells to prepare hybridomas; and selecting the hybridomas that produce monoclonal antibodies that specifically bind c-Met protein and. The animal that is immunized may be a mouse, a goat, a sheep, a guinea pig, a rat or a rabbit.

The immunizing may be performed using a method known in the art. For example, mice are immunized by emulsifying 1-100 μg immunogen per dose with an antigen adjuvant, such as a saline solution and/or Freund's adjuvant, in the same amount as that of the immunogen, and administering the antibody to the mice via a subcutaneous or intraperitoneal injection 2 to 6 times at intervals of every 2 to 5 weeks. 3 to 5 days after the final immunization of the mice, the spleen or lymphatic gland is taken out, and B cells from this tissue are fused with myeloma cells using a cell fusion method known in the art in the presence of a fusion facilitator. The fusion facilitator may be polyethylene glycol (PEG). The myeloma cells may be mouse-derived cells, such as P3U1, NS-1, P3x63. Ag 8.653, and Sp2/0-Ag14, or rat-derived cells, such as AG1 and AG2, but are not limited thereto. For example, the cell fusion method may be performed by mixing B cells and myeloma cells at a ratio of 1:1 to 10:1, adding 10-80% of PEG (molecular weight 1,000-6,000), and incubating the result at a temperature of about 30° C. to about 37° C. for about 1 to about 10 minutes. In addition, a hybridoma, which produces the monoclonal antibody specifically binding to c-Met protein, may be selected by culturing the hybridoma in a selective medium such as a hypoxanthine, aminopterin, thymidine (HAT) medium in which only the hybridoma survives, and measuring the antibody activity in the hybridoma culture supernatant using an enzyme-linked immunosorbent assay (ELISA) method. Finally, the hybridoma, which produces the monoclonal antibody specifically binding to c-Met protein, may be selected by repeatedly cloning by limiting dilution.

The monoclonal antibody may be an $IgG_1$, $IgG_2$, $IgG_3$, $IgG_4$, IgM, IgE, IgA1, $IgA_5$, or IgD-type antibody, for example, an IgG1-type antibody. In addition, the light chain constant region of the monoclonal antibody may have A or K type. The c-Met protein used as an antigen may be derived from humans or mice.

According to an embodiment of the invention, there is provided an antibody specifically binding to c-Met protein, the antibody having a heavy chain variable region including at least one heavy chain complementarity determining region (CDR) amino acid sequence selected from the group consisting of SEQ ID NO: 1, SEQ ID NO: 2, and SEQ ID NO: 3, and a light chain variable region including at least one light chain CDR amino acid sequence selected from the group consisting of SEQ ID NO: 5, SEQ ID NO: 6, and SEQ ID NO: 7. The antibody can be an antigen binding fragment of the antibody. In an embodiment, the heavy chain variable region comprises CDR amino acid sequences SEQ ID NO:1, SEQ ID NO:2, and SEQ ID NO:3. In an embodiment, the light chain variable region comprises CDR amino acid sequences SEQ ID NO:5, SEQ ID NO:6, and SEQ ID NO:7.

In an embodiment, the heavy chain variable region may be the amino acid sequence of SEQ ID NO: 4, and the light chain variable region may be the amino acid sequence of SEQ ID NO: 8.

According to an embodiment of the invention, there is provided an antibody specifically binding to c-Met protein, the antibody having a heavy chain variable region including at least one heavy chain CDR amino acid sequence selected from the group consisting of SEQ ID NO: 9, SEQ ID NO: 10, and SEQ ID NO: 11, and a light chain variable region including at least one light chain CDR amino acid sequence selected from the group consisting of SEQ ID NO: 13, SEQ ID NO: 14, and SEQ ID NO: 15, or antigen binding fragments thereof. In an embodiment, the heavy chain variable region comprises CDR amino acid sequences SEQ ID NO: 9, SEQ ID NO: 10, and SEQ ID NO: 11. In an embodiment, the light chain variable region comprises CDR amino acid sequences SEQ ID NO: 13, SEQ ID NO: 14, and SEQ ID NO: 15.

In an embodiment, the heavy chain variable region may be the amino acid sequence of SEQ ID NO: 8, and the light chain variable region may be the amino acid sequence of SEQ ID NO: 12.

The term "antibody" used herein refers to any protein moiety having immunoglobulin-like specific binding to an antigen, such as c-Met protein, and is understood to include a intact antibody and also any antigen binding fragment of an antibody.

The term "heavy chain" used herein is understood to include a full-length heavy chain including a variable region ($V_H$) having amino acid sequences that determine specificity for antigens and a constant region having three constant domains ($C_{H1}$, $C_{H2}$, and $C_{H3}$), and fragments thereof. In addition, the term "light chain" used herein is understood to include a full-length light chain including a variable region ($V_L$) having amino acid sequences that determine specificity for antigens and a constant region (CO; and fragments thereof.

The term "complementarity determining region (CDR)" used herein refers to an amino acid sequence found in the variable region of a heavy chain or a light chain of an immunoglobulin. The CDRs determine the specificity of an antibody and may provide a contact residue for binding to a specific epitope of an antigen. The heavy chain and the light chain may respectively include three CDRs (CDRH1, CDRH2, and CDRH3, and CDRL1, CDRL2, and CDRL3). Four framework regions, which have more highly conserved amino acid sequences than the CDRs, separate the CDR regions in the $V_H$ or $V_L$.

The term "antigen binding fragment" used herein refers to fragments of an intact immunoglobulin, and any part of a polypeptide including antigen binding regions having the ability to specifically bind to the antigen. For example, the antigen binding fragment may be a F(ab')$_2$ fragment, a Fab' fragment, a Fab fragment, a Fv fragment, or a scFv fragment, but is not limited thereto. A Fab fragment has one antigen binding site and contains the variable regions of a light chain and a heavy chain, the constant region of the light chain, and the first constant region $C_{H1}$ of the heavy chain. A Fab' fragment is different from the Fab fragment in that the Fab' fragment additionally includes the hinge region of the heavy chain, including at least one cysteine residue at the C-terminal of the heavy chain $C_{H1}$ region. The F(ab')$_2$ fragment is produced whereby cysteine residues of the Fab' fragment are joined by a disulfide bond at the hinge region. A Fv fragment is the minimal antibody fragment having only heavy chain variable regions and light chain variable regions, and a recombinant technique for producing the Fv fragment is well known in the art. Two-chain Fv fragments may have a structure in which heavy chain variable regions are linked to light chain variable regions by a non-covalent bond. Single-chain Fv fragments generally may have a dimer structure as in the two-chain Fv fragments in which heavy chain variable regions are covalently bound to light chain variable regions via a peptide linker or heavy and light chain variable regions are directly linked to each other at the C-terminal thereof. The antigen binding fragment may be obtained using a protease (for example, a whole antibody is digested with papain to obtain Fab fragments, and is digested with pepsin to obtain F(ab')$_2$ fragments), and may be prepared by a genetic recombinant technique.

The antibody may be a monoclonal antibody, a bispecific antibody, a non-human antibody, a human antibody, a humanized antibody, a chimeric antibody, single chain Fvs (scFV) fragments, a single chain antibody, Fab fragments, F(ab') fragments, disulfide-bond Fvs (sdFV) fragments, an anti-idiotype (anti-Id) antibody, and epitope-binding fragments of these antibodies, but is not limited thereto.

The antibody may be a humanized antibody or a human antibody. A humanized antibody of a non-human species, for example, mice, may be a chimeric immunoglobulin including minimal sequences derived from the immunoglobulin of mice, chains of the immunoglobulin, or fragments thereof, and may be, for example, Fv, Fab, Fab', F(ab')$_2$, or other antigen-binding subsequences of an antibody.

A non-human antibody is humanized using a method known in the art. In general, a humanized antibody has at least one amino acid residue introduced from a non-human donor. The humanization of a non-human antibody may be performed by replacing CDR sequences of a human antibody with corresponding CDR sequences of the non-human species, e.g., a rodent such as a mouse. Thus, a humanized antibody is a chimeric antibody, and a region that is smaller than the variable region of a substantially intact human antibody may be replaced by the corresponding sequences from a non-human antibody. For example, a humanized antibody may be a human antibody in which some CDR residues and possibly some framework (FR) residues are replaced by residues from the analogous CDR and FR sites in antibodies of a rodent.

A human antibody refers to an antibody having amino acid sequences of the variable and constant regions of the heavy and light chains derived from humans. The human antibody may be produced using technique known in the art, for example using a phage display library, a recombinant genetic technique, or cell engineering.

The effector regions of a human antibody may more successfully interact with other components of the human immune system. In addition, the human immune system does not recognize a human antibody as a foreign material. Thus the immune reaction against a human antibody introduced into a human may be less active than the immune reaction against full-length non-human antibodies or chimeric antibody fragments introduced into a human. Moreover, a human antibody introduced into a human has substantially the same half-life as that of endogenous human antibodies, and thus doses and times to be administered may be reduced.

The term "chimeric" used herein indicates that an antibody or the antigen binding site of an antibody (paratope) includes sequences derived from two different species.

The antibody specifically binding to c-Met protein or the antigen binding fragments thereof may include variants of the amino acid sequences disclosed herein within a range retaining the ability to specifically recognize c-Met protein. For example, to enhance the binding affinity and/or other biological properties of the antibody, the amino acid sequence of the antibody may be mutated. For example, such mutations include deletion, insertion, and/or substitution of amino acid sequence residues of the antibody. The amino acid mutations are made based on the relative similarity of amino acid side chain substituents with respect to, for example, hydrophobic properties, hydrophilic properties, charge, or size. For example, arginine, lysine, and histidine are each a positively charged residue; alanine, glysine, and serine have a similar size; and phenylalanine, tryptophan, and tyrosine have a similar shape. Therefore, based on the considerations described above, arginine, lysine, and histidine may be biologically functional equivalents, alanine, glycine, and serine may be biologically functional equivalents, and phenylalanine, tryptophan, and tyrosine may be biologically functional equivalents.

Amino acid substitution in a protein in which the activity of the molecules is not completely changed is well known in the art. The most common amino acid substitutions may be substitutions between similar amino acid residues, for example, between Ala and Ser, between Val and Ile, between Asp and Glu, between Thr and Ser, between Ala and Gly, between Ala and Thr, between Ser and Asn, between Ala and Val, between Ser and Gly, between Thy and Phe, between Ala and Pro, between Lys and Arg, between Asp and Asn, between Leu and Ile, between Leu and Val, between Ala and Glu, or between Asp and Gly. Considering mutations with biologically equivalent activity, the antibody specifically binding to c-Met protein or the antigen-binding fragments thereof may also be understood to include sequences substantially identical to the sequences disclosed herein. In this regard, a substantially identical amino acid sequence may be a sequence with at least 60% homology, at least 70% homology, at least 80% homology, or at least 90% homology to the amino acid sequences described in the sequence number, when the amino acid sequence of the sequence number and the other amino acid sequences are aligned to correspond to each other as much as possible, and the aligned amino acid sequences are analyzed using a commonly used algorithm known in the art. Alignment methods for sequence comparison are well known to one of ordinary skill in the art. For example, one of the sequence analysis programs available on the Internet at the NCBI Basic Local Alignment Search Tool (BLAST) home page, such as blastp, blastx, tblastn, or tblastx, may be used.

According to an embodiment of the invention, there is provided a polynucleotide encoding a heavy chain variable region of an antibody specifically binding to c-Met protein having an amino acid sequence of SEQ ID NO: 4.

In another embodiment, an isolated polynucleotide encodes an antibody heavy chain variable region comprising at least one heavy chain complementarity determining region (CDR) amino acid sequence selected from the group consisting of SEQ ID NO: 1, SEQ ID NO: 2, and SEQ ID NO: 3.

The polynucleotide may have a nucleotide sequence of SEQ ID NO: 17.

According to an embodiment of the invention, there is provided a polynucleotide encoding a light chain variable region of an antibody specifically binding to c-Met protein having an amino acid sequence of SEQ ID NO: 8.

In another embodiment, an isolated polynucleotide encodes an antibody light chain variable region comprising at least one light chain complementarity determining region (CDR) amino acid sequence selected from the group consisting of SEQ ID NO: 5, SEQ ID NO: 6, and SEQ ID NO: 7.

The polynucleotide may have a nucleotide sequence of SEQ ID NO: 18.

According to an embodiment of the invention, there is provided a polynucleotide encoding a heavy chain variable region of an antibody specifically binding to c-Met protein having an amino acid sequence of SEQ ID NO: 12.

In an embodiment, an isolated polynucleotide encodes an antibody heavy chain variable region comprising at least one heavy chain complementarity determining region (CDR) amino acid sequence selected from the group consisting of SEQ ID NO: 9, SEQ ID NO: 10, and SEQ ID NO: 11.

The polynucleotide may have a nucleotide sequence of SEQ ID NO: 19.

According to an embodiment of the invention, there is provided a polynucleotide encoding a light chain variable region of an antibody specifically binding to c-Met protein having an amino acid sequence of SEQ ID NO: 16.

In an embodiment, an isolated polynucleotide encodes an antibody light chain variable region comprising at least one light chain complementarity determining region (CDR) amino acid sequence selected from the group consisting of SEQ ID NO: 13, SEQ ID NO: 14, and SEQ ID NO: 15.

The polynucleotide may have a nucleotide sequence of SEQ ID NO: 20.

The term "polynucleotide" used herein refers to a polymer of deoxyribonucleic acid or ribonucleic acid that exists in a single-stranded or double-stranded form. The polynucleotide includes RNA genome sequences, DNA (gDNA and cDNA), and RNA sequences transcribed therefrom, and additionally includes analogues of natural polynucleotides, unless specifically mentioned.

The polynucleotide also includes nucleotide sequences encoding the amino acid sequences of the heavy or light chain variable regions of the antibody specifically binding to c-Met protein and nucleotide sequences complementary thereto. The complementary sequences include completely complementary sequences and substantially complementary sequences. For example, substantially complementary sequences are sequences that may be hybridized with the nucleotide sequences encoding the amino acid sequences of the heavy or light chain variable regions of the antibody specifically binding to c-Met protein under stringent conditions known in the art. Specifically, stringent conditions mean, for example, hybridization to DNA in 6×SSC at about 45° C., followed by one or more washes in 0.2×SSC/0.1% SDS at about 50° C.-65° C.

In addition, the nucleotide sequences encoding the amino acid sequences of the heavy and light chain variable regions may be mutated. The mutations include addition, deletion, non-conservative substitution, or conservative substitution of nucleotides. A polynucleotide encoding the amino acid sequence of a heavy or light chain variable region of an antibody specifically binding to c-Met protein is understood to include nucleotide sequences substantially identical to the nucleotide sequences described above. Substantially identical nucleic acid sequences may be sequences with at least 80% homology, at least 90% homology, or at least 95% homology to the above described nucleotide sequences, when the sequences are aligned to correspond to each other as much as possible, wherein the aligned nucleotide sequences are analyzed using any algorithm used in the art. Examples of sequence analysis programs are available on the Internet at the NCBI Basic Local Alignment Search Tool (BLAST) home page, for example, blastn.

According to an embodiment of the invention, there is provided a recombinant vector including a polynucleotide encoding a light chain variable region having an amino acid sequence of SEQ ID NO: 4 or a polynucleotide encoding a heavy chain variable region having an amino acid sequence of SEQ ID NO: 8. In some embodiments, the recombinant vector includes a polynucleotide encoding a light chain variable region having an amino acid sequence of SEQ ID NO: 4 and a polynucleotide encoding a heavy chain variable region having an amino acid sequence of SEQ ID NO: 8.

In an embodiment, the recombinant vector comprises an isolated polynucleotide encoding an antibody heavy chain variable region comprising at least one heavy chain complementarity determining region (CDR) amino acid sequence selected from the group consisting of SEQ ID NO: 1, SEQ ID NO: 2, and SEQ ID NO: 3; or an isolated polynucleotide encoding an antibody light chain variable region comprising at least one light chain complementarity determining region (CDR) amino acid sequence selected from the group consisting of SEQ ID NO: 5, SEQ ID NO: 6, and SEQ ID NO: 7.

In an embodiment, the recombinant vector comprises an isolated polynucleotide encoding an antibody heavy chain variable region comprising at least one heavy chain complementarity determining region (CDR) amino acid sequence selected from the group consisting of SEQ ID NO: 9, SEQ ID NO: 10, and SEQ ID NO: 11; or an isolated polynucleotide encoding an antibody light chain variable region comprising at least one light chain complementarity determining region (CDR) amino acid sequence selected from the group consisting of SEQ ID NO: 13, SEQ ID NO: 14, and SEQ ID NO: 15.

According to an embodiment of the invention, there is provided a recombinant vector including a polynucleotide encoding a light chain variable region having an amino acid sequence of SEQ ID NO: 12 or a polynucleotide encoding a heavy chain variable region having an amino acid sequence of SEQ ID NO: 16. In some embodiments, the recombinant vector includes a polynucleotide encoding a light chain variable region having an amino acid sequence of SEQ ID NO: 12 and a polynucleotide encoding a heavy chain variable region having an amino acid sequence of SEQ ID NO: 16.

The term "vector" used herein refers to a polynucleotide for expressing a target gene in a host cell. For example, the vector may include a plasmid vector, a cosmid vector, or a virus vector, such as a bacteriophage vector, an adenovirus vector, a retrovirus vector, and an adeno-associated virus vector. The recombinant vector may be prepared by manipulating a plasmid known in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4λB, λ-Charon, λΔz1, and M13), or a virus (for example, SV40).

In the recombinant vector, the polynucleotides encoding the amino acid sequences of the heavy and light chain variable regions may be operatively linked to a promoter. The term "operatively linked" used herein means a functional linkage between a nucleotide expression regulating sequence (for example, a promoter sequence) and other nucleotide sequences. Thus, the nucleotide expression regulating sequence may regulate the transcription and/or translation of the other nucleotide sequences.

The recombinant vector may be constructed for cloning or expression. The vector for expression may be a vector known in the art for expressing a foreign protein in a plant, animal, or microorganism. The recombinant vector may be constructed using various methods known in the art.

The recombinant vector may be constructed for use in prokaryotic or eukaryotic host cells. For example, when a prokaryotic cell is used as a host cell, the expression vector used generally includes a strong promoter capable of initiating transcription (for example, $p_L^\lambda$ promoter, trp promoter, lac promoter, tac promoter, T7 promoter), a ribosome binding site for initiating translation, and a transcription/translation termination sequence. When a eukaryotic cell is used as a host cell, the vector used generally includes the origin of replication acting in the eukaryotic cell, for example f1 origin of replication, SV40 origin of replication, pMB1 origin of replication, adeno origin of replication, AAV origin of replication, or BBV origin of replication, but is not limited thereto. A promoter in an expression vector for a eukaryotic host cell may be a promoter derived from the genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV). A transcription termination sequence in an expression vector for a eukaryotic host cell may be, in general, a polyadenylation sequence.

A vector system capable of expressing the heavy and light chain variable regions of the antibody may be a vector system in which the heavy and light chain variable regions are simultaneously expressed from a single vector, or a system in which the heavy and light chain variable regions are each independently expressed from separate vectors. In the latter case, the two vectors may be introduced into the host cell by co-transformation and targeted transformation.

According to an embodiment of the invention, there is provided a host cell including a polynucleotide encoding a light chain variable region having an amino acid sequence of SEQ ID NO: 4 and a polynucleotide encoding a heavy chain variable region having an amino acid sequence of SEQ ID NO: 8.

According to an embodiment of the invention, there is provided a host cell including a polynucleotide encoding a light chain variable region having an amino acid sequence of SEQ ID NO: 12 and a polynucleotide encoding a heavy chain variable region having an amino acid sequence of SEQ ID NO: 16.

For example, the host cell may be transformed with a recombinant vector including a polynucleotide encoding a light chain variable region having an amino acid sequence of SEQ ID NO: 4 and a polynucleotide encoding a heavy chain variable region having an amino acid sequence of SEQ ID NO: 8. The host cell may also be transformed with a recombinant vector including polynucleotide encoding a light chain variable region having an amino acid sequence of SEQ ID NO: 12 and polynucleotide encoding a heavy chain variable region having an amino acid sequence of SEQ ID NO: 16.

The host cell, which is capable of stably and consecutively cloning or expressing the recombinant vector, may be any host cell known in the art. A prokaryotic host cell may be a *Bacillus* genus bacterium, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*; or an intestinal bacterium, such as *Salmonella typhimurium*, *Serratia marcescens*, and various *Pseudomonas* species. A eukaryotic host cell may be a yeast (e.g., *Saccharomyces cerevisiae*), an insect cell, a plant cell, or an animal cell, for example, mouse Sp2/0, CHO (Chinese hamster ovary) K1, CHO DG44, PER.C6, W138, BHK, COS-7, 293, HepG2, Huh7, 3T3, RIN, or a MDCK cell line.

The polynucleotide or recombinant vector including the same may be transferred into the host cell using methods known in the art. For example, when a prokaryotic cell is used as the host cell, the transfer may be performed using a $CaCl_2$ method or an electroporation method, and when a eukaryotic cell is used as the host cell, the transfer may be performed by microinjection, calcium phosphate precipitation, electroporation, liposome-mediated transfection, or gene bombardment, but is not limited thereto.

When a microorganism, such as *E. coli*, is used as the host cell, the production of antibodies is higher than that in an animal cell. However, a microorganism is not suitable for producing intact Ig-type antibodies due to lack of glycosylation of the antibodies produced, although a microorganism may be used for producing antigen-binding fragments of an antibody such as Fab and Fv.

A transformed host cell may be selected using a phenotype expressed by a selectable marker by any method known in the art. For example, when the selectable marker is a specific antibiotic resistance gene, a transformant is cultured in a medium including the antibiotic, and thus the transformant may easily be selected.

According to an embodiment of the invention, there is provided a hybridoma cell having Accession Number:

KCLRF-BP-00219 that produces a monoclonal antibody specifically binding to c-Met protein.

According to an embodiment of the present invention, there is provided a hybridoma cell having Accession Number: KCLRF-BP-00223 that produces a monoclonal antibody specifically binding to c-Met protein.

A method of preparing the hybridoma cell will be described in detail below. The hybridoma cell lines prepared in the following Examples have been deposited in the Korean Cell Line Bank (Cancer Research Institute, Seoul National University College of Medicine, 28 Yongon-dong, Chongno-Gu, Seoul, 110-744, Korea), which is an international depository authority under the Budapest Treaty, as of 9 Oct. 2009 and 21 Oct. 2009 for Accession Number: KCLRF-BP-00219 and Accession Number: KCLRF-BP-00223, respectively. The deposited hybridoma cell lines are kept according to the requirements of the Budapest Treaty for the deposit of a microorganism, and are available for distribution to the general public upon request.

According to an embodiment of the invention, there is provided a kit for diagnosing or detecting cancer. The kit includes an antibody specifically binding to c-Met protein and can be used to measure the degree of expression of c-Met in a sample through an antigen-antibody binding reaction.

The c-Met protein is over-expressed in many kinds of cancers as shown in Table 1 below. In particular, it is known that most cancer cases in which the patients have a poor prognosis are characterized by over-expression of c-Met protein. In Table 1, "O" in a column corresponds to the cancer having the property while an "X" corresponds to the cancer not having the property.

TABLE 1

| Kinds of cancers | c-Met over-expression | Poor prognosis |
| --- | --- | --- |
| Bladder cancer | O | O |
| Breast cancer | O | O |
| Cervical cancer | O | O |
| Cholangiocarcinoma | O | X |
| Large intestine cancer | O | O |
| Endometrial cancer | O | X |
| Esophageal cancer | O | O |
| Stomach cancer | O | O |
| Head and neck cancer | O | O |
| Kidney cancer | O | O |
| Liver cancer | O | O |
| Lung cancer | O | O |
| Nasopharyngeal cancer | O | O |
| Ovarian cancer | O | O |
| pancreatic/gallbladder cancer | O | X |
| Prostatic carcinoma | O | O |
| Thyroid cancer | O | O |
| Osteosarcoma | O | X |
| Rhabdomyosarcoma | O | O |
| Synovial sarcoma | O | O |
| Kaposi's sarcoma | O | X |
| Leiomyosarcoma | O | O |
| Malignant fibrous histiocytoma/fibrosarcoma | O | X |
| Acute myeloid leukemia | X | X |
| Adult T-cell leukemia | O | O |
| Chronic myelogeneous leukemia | X | X |
| Lymphoma | O | O |
| Multiple myeloma | O | O |
| glioblastoma/astrocytoma | O | O |
| Melanoma | O | O |
| Mesothelioma | O | O |
| Wilms' tumor | O | X |

Thus, examples of the cancer that may be diagnosed or detected using the kit may include carcinoma, lymphoma, blastoma, and leukemia. More specifically, examples of the cancer diagnosed or detected may be bladder cancer, breast cancer, cervical cancer, cholangiocarcinoma, large intestine cancer, endometrial cancer, esophageal cancer, stomach cancer, head and neck cancer, kidney cancer, liver cancer, lung cancer, nasopharyngeal cancer, ovarian cancer, pancreatic cancer, gallbladder cancer, prostatic carcinoma, thyroid cancer, osteosarcoma, rhabdomyosarcoma, synovial sarcoma, Kaposi's sarcoma, leiomyosarcoma, malignant fibrous histiocytoma, fibrosarcoma, acute myeloid leukemia, adult T-cell leukemia, lymphoma, multiple myeloma, glioblastoma/astrocytoma, melanoma, mesothelioma, and Wilms' tumor, but the cancer is not limited thereto.

The kit may be used in diagnosing or detecting cancer by detecting c-Met protein through an antigen-antibody binding reaction, and may be a kit that may be used in any analysis method for detecting the presence of c-Met protein by interaction with an antibody disclosed herein. Kits are well-known to those of ordinary skill in the art, and may easily be re-configured by one of ordinary skill in the art to include appropriate reagents in addition to an antibody specifically binding to c-Met protein disclosed herein. For example, the kit may include an antibody, or antigen-binding fragment thereof, disclosed herein and a control cell in which c-Met protein is over-expressed. For example, the kit may be a kit for diagnosing or detecting cancer by immunohistochemistry, immunoblot, immunoprecipitation, ELISA, or radioimmunoassay (RIA), but is not limited thereto. The antibody may be any antibody specifically binding to c-Met protein disclosed herein.

In an embodiment, the antibody may be an antibody that has a heavy chain variable region including at least one heavy chain CDR amino acid sequence selected from the group consisting of SEQ ID NO: 1, SEQ ID NO: 2, and SEQ ID NO: 3. In some embodiments, the antibody further includes a light chain variable region including at least one light chain CDR amino acid sequence selected from the group consisting of SEQ ID NO: 5, SEQ ID NO: 6, and SEQ ID NO: 7. In an embodiment, the antibody has a heavy chain variable region including each of the three heavy chain CDR amino acid sequences consisting of SEQ ID NO: 1, SEQ ID NO: 2, and SEQ ID NO: 3 or a light chain variable region including each of the three light chain CDR amino acid sequences consisting of SEQ ID NO: 5, SEQ ID NO: 6, and SEQ ID NO: 7.

In an embodiment, the antibody has a heavy chain variable region including at least one heavy chain CDR amino acid sequence selected from the group consisting of SEQ ID NO: 9, SEQ ID NO: 10, and SEQ ID NO: 11. In some embodiments, the antibody further comprises a light chain variable region including at least one light chain CDR amino acid sequence selected from the group consisting of SEQ ID NO: 13, SEQ ID NO: 14, and SEQ ID NO: 15. In an embodiment, the antibody has a heavy chain variable region including each of the three heavy chain CDR amino acid sequences consisting of SEQ ID NO: 9, SEQ ID NO: 10, and SEQ ID NO: 11 or a light chain variable region including each of the three light chain CDR amino acid sequences consisting of SEQ ID NO: 13, SEQ ID NO: 14, and SEQ ID NO: 15.

The antibody specifically binding to c-Met protein may be prepared using a method known in the art, such as a fusion method, a recombinant DNA method, or a phage antibody library method. A general method of preparing an antibody is described above.

The kit for diagnosing or detecting cancer may be prepared using any method known in the art. In some embodiments, the kit may include a freeze-dried antibody, a buffer solution, a stabilizing agent, and an inactive protein. A detailed description for detecting c-Met protein with the antibody, such as any method described herein, may be provided as a protocol included with the kit.

According to an embodiment of the invention, there is provided a method of detecting c-Met protein, the method includes contacting a sample isolated from a subject with an antibody specifically binding to c-Met protein. The method may provide information regarding c-Met expression level in the sample needed for diagnosis, staging, or detection of cancer.

The sample isolated from a subject may be a sample isolated from a patient with cancer or a normal person. In an embodiment, the sample may include tumor cells from a patient with cancer to assess the level of over-expression of c-Met protein in order to permit staging of the patient's cancer. In an embodiment, the sample is a cell or tissue isolated from a human to detect the presence or absence of cancer in the sample or to determine whether there is a risk of the development of the cancer in the sample.

In some embodiments, the cancer detected, staged or assessed for risk of development due to over-expression of c-Met protein is a cancer shown in Table 1 above. The contacting may be performed by contacting the antibody specifically binding to c-Met protein with the sample such that if the antigen c-Met protein exists in the sample the antibody will specifically bind the c-Met protein.

The antigen-antibody binding reaction may be performed using various immunoassay methods or immunostaining methods known in the art. Examples of immunoassay or immunostaining methods are radioimmunoassay, radioimmunoprecipitation, immunoprecipitation, ELISA, capture-ELISA, inhibition or competition assay, sandwich analysis, flow cytometry, immunofluorescence staining, and immunoaffinity purification, but are not limited thereto. For example, in an embodiment of a radioimmunoassay method, a radioisotope-labeled antibody may be used to detect c-Met protein. The radioisotope may be, for example, $C^{14}$, $I^{125}$, $P^{32}$ or $S^{35}$.

In an embodiment of an ELISA method, the method may include: (i) coating a surface of a solid substrate with a cell sample extract to be analyzed; (ii) incubating the cell sample extract with an antibody specifically binding to c-Met protein as a first antibody; (iii) incubating the resultant product with a secondary antibody conjugated to an enzyme; and (iv) measuring the activity of the enzyme.

The solid substrate may be a hydrocarbon polymer such as polystyrene or polypropylene, glass, a metal or a gel. For example, the solid substrate may be a microtiter plate. The enzyme conjugated to a secondary antibody may be an enzyme catalyzing a colorimetric, fluorometric, luminescence or infra-red reactions, but is not limited thereto. For example, the enzyme may be alkaline phosphatase, β-galactosidase, horseradish peroxidase, luciferase, or Cytochrome $P_{450}$. When alkaline phosphatase is used, bromo-chloro-indolyl-phosphate (BCIP), nitro blue tetrazolium (NBT), naphthol-AS-B1-phosphate, or enhanced chemifluorescence (ECF) may be used as a substrate. When horseradish peroxidase is used, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), hypersensitive reaction solution (HYR: p-phenylenediamine-HCl and pyrocatechol), tetramethylbenzidine (TMB), 2,2'-Azine-di[3-ethyl-benzthiazoline sulfonate] (ABTS), o-phenylenediamine (OPD) and naphtol/pyronin, glucose oxidase and t-nitroblue tetrazolium (t-NBT), or m-phenzaine methossulfate (m-PMS) may be used as a substrate.

The antibody specifically binding to c-Met protein may have a label generating a detectable signal. The label may be a chemical label such as biotin; an enzymatic label such as alkaline phosphatase, β-galactosidase, horseradish peroxidase and Cytochrome $P_{450}$, a radioactive label such as $C^{14}$, $I^{125}$, $P^{32}$ and $S^{35}$; a fluorescent label such as fluorescein; a luminescent label; a chemiluminescent label; or a fluorescence resonance energy transfer (FRET) label, but is not limited thereto.

The final measurement of enzyme activities or signals in the ELISA method may be performed by any method known to one skilled in the art to enable quantitative or qualitative analysis of c-Met protein amounts present in the sample. Signals could be detected easily by streptavidin in the case of a biotin-labeled antibody and by luciferin in the case of a luciferase-labeled antibody.

When an immunohistochemistry method is used, the method may include: (i) immobilizing a cell or tissue sample to be analyzed and sectioning thereof; (ii) incubating the section with an antibody specifically binding to c-Met protein as a first antibody; (iii) reacting the resultant product with a secondary antibody conjugated to an enzyme; and (iv) measuring the activity of the enzyme.

Methods for immobilizing and sectioning the sample are well known in the art. For example, the sample may be immobilized using a chemical material such as formalin. In addition, the section may be produced after the sample is embedded in a material such as paraffin. When paraffin is used in the production of the section, paraffinization may be performed to easily react an antigen in the cell or tissue sample with the first antibody.

The operations (iii) and (iv) have already been described above with respect to the ELISA method.

The cancer may be diagnosed, staged, or detected by analyzing the intensity of final signals from the immunoassay. In other words, when, for example, the s c-Met protein signal in a sample is stronger than the c-Met signal of a normal control sample, the sample may be determined to have cancer present and therefore the subject from whom the sample was obtained may be diagnosed as having cancer.

The antibody specifically binding to c-Met protein may be any antibody, or antigen-binding fragment, specifically binding to c-Met protein disclosed herein, for example a monoclonal antibody produced in the hybridoma cell having accession number KCLRF-BP-00219 or KCLRF-BP-00223.

According to an embodiment of the invention, there is provided a composition for preventing or treating an angiogenesis-related disease or cancer. The composition includes an antibody that specifically binds c-Met protein, or an antigen binding fragment thereof, disclosed herein; and a pharmaceutically acceptable excipient. The antibody or antigen binding fragment may be present in a therapeutically effective amount.

The composition may be used to prevent or treat cancer. Examples of the cancer include carcinoma, lymphoma, blastoma, sarcoma, and leukemia. In particular, the cancer may be squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, or various types of head and neck cancers, but is not limited thereto.

In addition, the composition may be used to prevent or treat an angiogenesis-related disease. Angiogenesis is a physiological process involving the formation of new capillary vessels from pre-existing vessels. If angiogenesis is not controlled autonomously, the vessels grow abnormally, causing diseases. Examples of an angiogenesis-related disease are rheumatoid arthritis, osteoarthritis, septic arthritis, psoriasis, corneal ulcer, age-related macular degeneration, diabetic retinopathy, proliferative vitreoretinopathy, premature retinopathy, keratoconus, Sjogren's syndrome, myopia ocular tumors, corneal graft rejection, abnormal wound healing, bone diseases, proteinuria, abdominal aortic aneurysm diseases, degenerative cartilage loss due to traumatic joint damage, nervous system demyelinating diseases, liver cirrhosis, glomerular diseases, premature rupture of embryonic membranes, inflammatory bowel disease, periodontal disease, arteriosclerosis, restenosis, central nervous system inflammation diseases, Alzheimer's disease, skin aging, and cancer invasion and metastasis, but are not limited thereto.

The antibody or antigen binding fragment thereof may be an antibody specifically binding to c-Met protein, or antigen binding fragments thereof, that has a heavy chain variable region including at least one heavy chain CDR amino acid sequence selected from the group consisting of SEQ ID NO: 1, SEQ ID NO: 2, and SEQ ID NO: 3, and a light chain variable region including at least one light chain CDR amino acid sequence selected from the group consisting of SEQ ID NO: 5, SEQ ID NO: 6, and SEQ ID NO: 7; or an antibody specifically binding to c-Met protein, or antigen binding fragments thereof, that has a heavy chain variable region including at least one heavy chain CDR amino acid sequence selected from the group consisting of SEQ ID NO: 9, SEQ ID NO: 10, and SEQ ID NO: 11, and a light chain variable region including at least one light chain CDR amino acid sequence selected from the group consisting of SEQ ID NO: 13, SEQ ID NO: 14, and SEQ ID NO: 15.

In some embodiments, the antibody specifically binding to c-Met protein may be a monoclonal antibody produced in a hybridoma cell having accession number KCLRF-BP-00219 or KCLRF-BP-00223.

The antibody or antigen binding fragment thereof may act as an antagonist with respect to the c-Met protein.

The term "antagonist" is used in the broadest sense herein, and is understood to include all molecules that partially or entirely block, inhibit, and/or neutralize at least one biological activity of a target (for example, c-Met). For example, the term "antagonist antibody" refers to an antibody that inhibits or decreases the biological activity of an antigen, for example c-Met, that the antibody binds. In some embodiments, the antibody or the antigen binding fragment thereof specifically binds the extracellular region of the c-Met protein to block transduction of signals in a cell, thereby, for example, inhibiting proliferation of tumor cells. Thus, the antibody or the antigen binding fragment thereof may treat cancer. In addition, the antibody or the antigen binding fragment thereof may inhibit angiogenesis through the mechanism described above. The treatment of cancer and the inhibition of angiogenesis by the antibody or the antigen binding fragment thereof may be performed independently or simultaneously.

The composition for preventing or treating angiogenesis-related diseases or cancers includes a pharmaceutically acceptable excipient. The pharmaceutically acceptable excipient, which is commonly used in formulation, may be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, or mineral oil, but is not limited thereto. The composition may further include a lubricant, a wetting agent, a sweetener, a flavor enhancer, an emulsifying agent, a suspension agent, or a preservative.

The composition for preventing or treating an angiogenesis-related disease or cancer may be administered orally or parenterally. Parenteral administration may include intravenous injection, subcutaneous injection, muscular injection, intraperitoneal injection, endothelial administration, local administration, intranasal administration, intrapulmonary administration, and rectal administration. Since oral administration leads to digestion of protein or peptide, the composition may be coated or otherwise formulated to prevent digestion of the antibody. In addition, the composition may be administered by a device capable of targeting the composition to a particular cells.

A suitable dose of the composition for preventing or treating an angiogenesis-related disease or cancer may depend on many factors, such as formulation methods, administration methods, ages of patients, body weight, gender, pathologic conditions, diets, administration time, administration route, excretion speed, and reaction sensitivity. A desirable dose of the composition may be in the range of about 0.001 to about 100 mg/kg for an adult. The term "therapeutically effective amount" used herein refers to a sufficient amount used in preventing or treating cancer or an angiogenesis-related disease.

The composition may be formulated with a pharmaceutically acceptable excipient and/or an additive by any method known in the art. The composition may be prepared in a unit dose form or may be contained in a multi-dose container. The formulation may be a solution in oil or an aqueous medium, a suspension, a syrup, an emulsifying solution, an extract, powder, granules, a tablet, or a capsule, and may further include a dispersing or a stabilizing agent. In addition, the composition may be administered as an individual drug, or together with other drugs, and may be administered sequentially or simultaneously with other drugs.

The composition may be formulated as an immunoliposome, that is, a liposome that includes as a targeting ligand an antibody-derived protein. The liposome including the antibody may be prepared using a method known in the art. A liposome is a lipid composition including, for example, phosphatidylcholine, cholesterol, and polyethyleneglycol-derived phosphatidylethanolamine, and may be prepared, for example, by a reverse phase evaporation method. For example, Fab' fragments of an antibody may be adhered to the liposome through a thiol-disulfide exchange reaction. A chemical drug, such as doxorubicin, may be further included in the liposome.

According to an embodiment of the invention, there is provided a method of treating an angiogenesis-related disease or a cancer of a subject, the method including administering to the subject having an angiogenesis-related disease or cancer a therapeutically effective amount of an antibody specifically binding to c-Met protein or an antigen binding fragment thereof. The antibody or antigen binding fragment thereof may be in the form of a composition including a pharmaceutically acceptable excipient.

The antibody or antigen binding fragment thereof may be an antibody specifically binding to c-Met protein that has a heavy chain variable region including at least one heavy chain CDR amino acid sequence selected from the group consisting of SEQ ID NO: 1, SEQ ID NO: 2, and SEQ ID NO: 3, and a light chain variable region including at least one light chain CDR amino acid sequence selected from the group consisting of SEQ ID NO: 5, SEQ ID NO: 6, and SEQ ID NO: 7, or antigen binding fragments thereof; or an antibody specifically binding to c-Met protein that has a heavy chain variable region including at least one heavy chain CDR amino acid sequence selected from the group consisting of SEQ ID NO: 9, SEQ ID NO: 10, and SEQ ID NO: 11, and a light chain variable region including at least one light chain CDR amino acid sequence selected from the group consisting of SEQ ID NO: 13, SEQ ID NO: 14, and SEQ ID NO: 15, or antigen binding fragments thereof.

A detailed description of the composition for preventing or treating an angiogenesis-related disease or cancer and administration methods thereof have been provided above.

The subjects to which the antibody is administered includes animals. For example, the animals may be humans, dogs, cats, or mice.

According to an embodiment of the invention, there is provided an animal model for a cancer or an angiogenesis-related disease that is prepared by inoculating the animal with a c-Met expressing cancer cell line to form a cancer therein, and in which, when an antibody specifically binding to c-Met protein or an antigen binding fragment thereof, is administered to the animal model, the angiogenesis or the formation or growth of tumor cells is inhibited.

The cancer formed in the animal model may be at least one selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, and various types of head and neck cancers.

The tumor cells may be tumor cells derived from the same species as those of the animal model or tumor cells derived from different animal species. For example, the tumor cells may be human U87-MG glioblastoma cells. The animal model may be any animal except for humans. The animal may be a mammal, for example, mice. By using the animal model to test the efficacy of the treatment method, it can be determined whether the angiogenesis-related disease or cancer is treated by an antibody, or an antigen binding fragment thereof, disclosed herein.

One or more embodiments of the invention will now be described in further detail with reference to the following examples. However, these examples are for illustrative purposes only and are not intended to limit the scope of the invention.

Example 1

Preparation of Hybridomas that Produce a Monoclonal Antibody Specifically Binding c-Met and Production of the Monoclonal Antibodies AbF24 and Stan34

The process of producing the hybridoma cell clones and obtaining monoclonal antibody, described below, is schematically illustrated in FIG. 1.

(1) Immunization of Mice

Five 4 to 6-week-old BALB/c mice (Japan SLC, Inc.) were each given an intraperitoneal injection of 0.100 μg human c-Met/Fc fusion protein (R&D Systems, Inc.) emulsified in complete Freund's adjuvant. After two weeks, each mouse were again administered an intraperitoneal injection of 50 μg human c-Met/Fc fusion protein in incomplete Freund's adjuvant. After an additional week, a final boosting with the antigen in incomplete Freund's adjuvant was performed. Blood was collected from the tail of each mouse three days after the final boosting to obtain serum, which was diluted at 1/1000 with phosphate buffered saline (PBS) and subjected to an enzyme-linked immunosorbent assay (ELISA) to determine the titer of antibodies recognizing c-Met. From the results, mice in which a sufficient amount of the antibody was obtained were selected for performing cell fusion.

(2) Cell Fusion and Preparation of Hybridoma Cells

A mixture of 50 μg human c-Met/Fc fusion protein in PBS was administered via intraperitoneal injection to the mice. After three days, each immunized mice was anesthetized, and the spleen was removed from each mouse. The extracted spleen was ground with a mesh to isolate cells, which were mixed with Dulbecco's Modified Eagle medium (DMEM) to prepare a spleen cell suspension. The suspension was centrifuged to collect the cell layer. Then, $1 \times 10^8$ spleen cells were mixed with $1 \times 10^8$ mouse myeloma cells (Sp2/0) and centrifuged to precipitate the cells. The precipitate was slowly dispersed, and treated with 1 ml of 45% polyethylene glycol (PEG) in DMEM. The resultant was incubated at 37° C. for one minute, and 1 ml DMEM was then added. Subsequently, 10 ml DMEM was added to the resultant for 1 minute, and incubated in a water bath at 37° C. for 5 minutes. The resultant was re-centrifuged after the total volume of the cell suspension was made to reach 50 ml. The resulting cell precipitate was re-suspended in hypoxanthine aminopterin thymidine medium (HAT medium) at a concentration of $1–2 \times 10^5$ cells/ml. Then, 0.1 ml was aliquots were distributed into the wells of a 96-well plate and incubated in a carbon dioxide incubator at 37° C. to prepare hybridoma cells.

(3) Selection of Hybridoma Cells that Produce Monoclonal Antibodies Against to c-Met Protein The hybridoma cells prepared above in (2) were screened by ELISA analysis to select for those producing antibodies specific for c-Met protein using human c-Met/Fc fusion protein and human Fc protein as antigens.

50 μl (2 μg/ml) of human c-Met/Fc fusion protein was added to each well of a microtiter plate to attach to the surface of the microtiter plate, and unreacted antigen was removed by washing. To select and exclude antibodies binding to Fc, and not to c-Met, human Fc protein was also attached to the surface of each well of the microtiter plate using the same method.

50 μl of a hybridoma cell culture was added to each well of the microtiter plate and incubated with the attached antigens for 1 hour. Then, the wells were washed with Tris-buffered saline TWEEN-20 (TBST) solution to remove unbound cells. Goat anti-mouse IgG-horseradish peroxidase (IgG-HRP) was added to the wells, incubated at room temperature for 1 hour and then wells were washed with TBST solution. Subsequently, a solution of o-phenylenediamine dihydrochloride (OPD), a substrate for colorimetric detection of HRP activity in ELISA was added to the wells, and the degree of reaction was evaluated by measuring absorption at 450 nm using an ELISA reader. In such a manner, repeated selection of hybridoma cell lines that produce an antibody that does not bind human Fc and which highly specifically binds human c-Met protein was performed. A limiting dilution was performed on the selected hybridoma cell lines to finally obtain two hybridoma cell line clones, each producing a monoclonal antibody specific for c-MET. The two hybridoma cell lines, named SAIT-MET-AbF24 (AbF24) and SAIT-MET-Stan34 (Stan34), were deposited in the Korean Cell Line Bank and received accession number KCLRF-BP-00219 and accession number KCLRF-BP-00223, respectively.

(4) Production and Purification of Monoclonal Antibody

The hybridoma cells obtained in (3) above were cultured in serum-free medium to produce monoclonal antibodies for purification from the culture.

AbF24 hybridoma cells cultured in 50 ml DMEM including 10% fetal bovine serum (FBS) were centrifuged to obtain a cell precipitate. The cell precipitate was washed more than twice with 20 ml PBS to remove the FBS. The cell precipitate was re-suspended in 50 ml DMEM and then incubated in a carbon dioxide incubator at 37° C. for 3 days. Subsequently, the cell culture was centrifuged to precipitate the antibody-producing cells. The culture medium including antibodies was removed and either stored at 4° C. or used directly. Antibodies were further purified from 50 to 300 ml of the culture medium using a AKTA purification device (GE Health) equipped with an affinity column (protein G agarose column; Pharmacia, USA). The purified antibodies were stored after replacing the supernatant with PBS using a filter for protein aggregation (Amicon) to be used in a subsequent process.

The monoclonal antibody Stan34 was produced from Stan34 hybridoma cells and purified using the same procedures.

Example 2

Determination of Isotypes of Monoclonal Antibodies AbF24 and Stan34

An ELISA experiment was performed to determine the isotype of the two antibodies prepared in Example 1 using a BD Pharmingen™ Mouse Immunoglobulin Isotyping ELISA kit (BD Biosciences). The results of the assay are summarized in Table 2 below. From the results, the monoclonal antibody AbF24 is determined to have the highest reaction value, i.e., 2703.0, with the IgG1-specific antibody and the light chain was determined to be a k type. In addition, the monoclonal antibody Stan34 is determined to have the highest reaction value, i.e., 567.5, with the IgG1-specific antibody and the light chain was determined to be a k type (refer to Table 2).

TABLE 2

| mAb | IgA | IgE | IgG1 | IgG2a | IgG2b | IgG3 | IgM | determination | Light chain |
|---|---|---|---|---|---|---|---|---|---|
| AbF24 | 10.0 | 44.5 | 2703.0 | 3.0 | 10.0 | 4.0 | 5.0 | 2703.0 IgG1 | κ |
| Stan34 | 5.5 | 45.0 | 567.5 | 4.0 | 7.0 | 1.0 | 1.0 | 567.5 IgG1 | κ |

Example 3

Determination of Recognition of c-MET from Different Species by Monoclonal Antibody AbF46

ELISA was used to determine whether the monoclonal antibodies AbF24 and Stan34 against human c-Met protein recognized mouse c-Met.

First, 50 µl (2 ug/ml) of human or mouse c-Met/Fc fusion protein (R&D Systems, Inc.) was added a well of a plate. Unreacted antigen was removed by washing. Then, 50 ng of purified monoclonal antibody AbF24 or Stan34 was added to each well and incubated with the antigen for 1 hour. Then, the well was washed with TBST to remove unreacted antibody. Goat anti-mouse IgG-HRP was added to the well, incubated at room temperature for 1 hour, and then was washed with TBST solution. Subsequently, OPD solution was added, and the degree of peroxidase reaction was evaluated by measuring absorption at 450 nm using an ELISA reader (Bio-Rad). It was determined that the monoclonal antibody AbF24 bound to the human c-Met and to the mouse c-Met protein.

Additionally, a commonly used monoclonal antibody against human c-Met, 5D5 (Genetech), was tested. Results of the ELISA are shown in Table 3 below. For the antibody 5D5, the specific recognition and binding to mouse c-Met protein is low compared to recognition and binding of human c-Met. In contrast, the monoclonal antibodies AbF24 and Stan34 were each determined to recognize specifically both human and mouse c-Met protein (refer to Table 3). Thus, the monoclonal antibodies AbF24 and Stan34 may be used in experiments using a mouse model, such as in vivo imaging.

TABLE 3

| Antigen | 5D5 | AbF24 | Stan34 |
|---|---|---|---|
| Human c-Met/Fc | 0.3729 | 0.2619 | 0.4763 |
| Mouse c-Met/Fc | 0.1126 | 0.3541 | 0.481 |

Example 4

Immunoprecipitation of c-Met Using Monoclonal Antibodies AbF24 and Stan34

Cultured HEK293 cells endogenously express c-Met at only a low level. An immunoprecipitation experiment was performed to determine whether monoclonal antibodies AbF24 and Stan34 recognized expressed c-Met on the cells.

Figure 2:
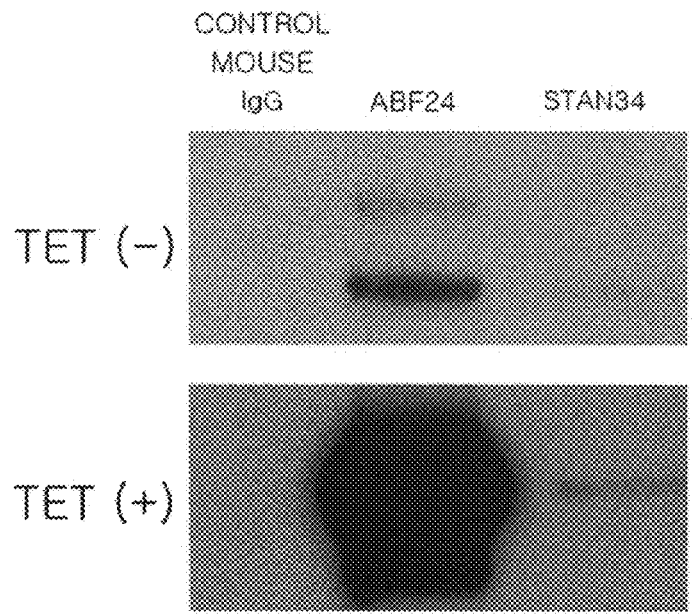
FIG. 2 presents images showing immunoprecipitation results with HEK293 cells in which the expression level of c-Met is tetracycline (Tet)-regulated and using antibodies AbF24 and Stan34, which recognize c-Met, and a control mouse antibody, according to an embodiment of the invention.

A gene encoding c-Met was cloned into the vector, pcDNA5/FRT/TO (Invitrogen) which is designed for tetracycline-regulated expression, and the resultant vector was transfected into HEK293 cells (Korea Cell Line Bank). The transfected cell line was cultured in DMEM including 10% (v/v) of fetal bovine serum and 1 µg/ml tetracycline overnight to increase expression of c-Met. The cultured cell line was washed with 20 mM Hepes, 150 mM NaCl; pH 7.5 (HBS), and then treated with a lysis buffer solution (20 mM Hepes, 150 mM NaCl, 1% Triton X-100, 1 mM DTT, 10 mM NaF, 2 mM $Na_2VO_4$, 10 µg each of the PCL protease inhibitors pepstatin, chymostatin, and leupeptin/ml, 1 mM phenylmethylsulfonyl fluoride (PMSF); pH 7.5) to collect cells. The collected cells (20 µl) were fragmented by ultrasonic waves and centrifuged at 12,000 rpm to obtain the supernatant. Immunoprecipitation was performed by mixing the supernatant with 300 µl HBS, and then 8 µl Dyna G beads (Dynal) and 2 µg antibody, were added to the mixture. AbF24, Stan34, or mouse IgG (control) was used as the antibody in the immunoprecipitations. The resultant product was then agitated at 4° C. for 45 minutes. The beads were removed from the supernatant, washed three times with a washing buffer solution (20 mM Hepes, 150 mM NaCl, 0.5% NP-40; pH 7.5), and then washed twice with HBS. Then, bound c-Met protein was removed from the beads and subjected to SDS-polyacrylamide gel electrophoresis, followed by transfer, and Western blot analysis using an anti-c-Met antibody (Santa Cruz) with detection by Electrochemiluminescence (ECL). FIG. 2 presents the Western blot results of immunoprecipitation by control mouse IgG, AbF24, or Stan 34 of lysates of the transfected HEK293 cells cultured in the presence (lower panel) or absence (upper panel) of tetracycline. As illustrated in FIG. 2, the monoclonal antibody AbF24 recognized and immunoprecipitated intrinsic c-Met and over-expressed c-Met in the HEK293 cell line. More c-Met protein was present in the cells cultured with tetracycline. The upper band seen in the AbF24 lane is unprocessed c-Met. FIG. 2 shows that Stan34 is also able to immunoprecipitate c-Met, however under these conditions fainter bands of c-Met were obtained from both cell lysates with Stan34 compared to with AbF24. No immunoprecipitation of c-Met by the control mouse IgG was observed.

Example 5

Immunohistochemistry Staining Reaction of c-Met Using Monoclonal Antibodies AbF24 and Stan34 in a Sample from a Patient with Cancer A tumor tissue sample and a normal tissue sample isolated from a patient with cancer were each embedded in paraffin to obtain a cell block. Each cell block was sliced to a thickness of 50 μm and attached to a slide. Then, the paraffin was removed with xylene for 10 minutes, the resultant product was rehydrated with 100% ethanol for three minutes and 95% ethanol for 1 minute, and then washed with distilled water for 1 minute. To recover antigenicity, the cell block slide was treated with 0.02 mg/ml protease K at 37° C. for four minutes. To remove endogenous peroxidase activity, the slide was incubated in a peroxidase blocking solution (Dako) for 10 minutes, and then washed with TBST buffer solution for four minutes. The slide was incubated for five minutes with a blocking antibody to eliminate non-specific immune reactions and then washed with the TBST buffer solution. The resulting product was treated with 10 μg/ml of either monoclonal antibody AbF24 or monoclonal antibody Stan34 as a first antibody, stored for 90 minutes, and then washed with the TBST buffer solution. Next, the resulting product was treated with a secondary antibody, HRP (Horse Radish Peroxidase)-goat anti-human IgG conjugate (Zymed), stored for 20 minutes, and then washed with TBS. The resulting product was visualized using diaminobenzidine (DAB) under a microscope. Subsequently, the resulting product was counter stained with Mayer's hematoxylin, mounted with a mounting medium, and read under an optical microscope. Brown color represents the location of c-Met molecules detected by DAB and blue color represents nuclei stained by hematoxylin. Images of immunohistochemically stained tumor and normal cell samples using AbF24, Stan34, and a commercially available mouse anti-c-MET monoclonal antibody (Zymed, Product No: 37-0100) are shown in FIGS. 3A, 3B, and 3C, respectively.

Figure 3A:
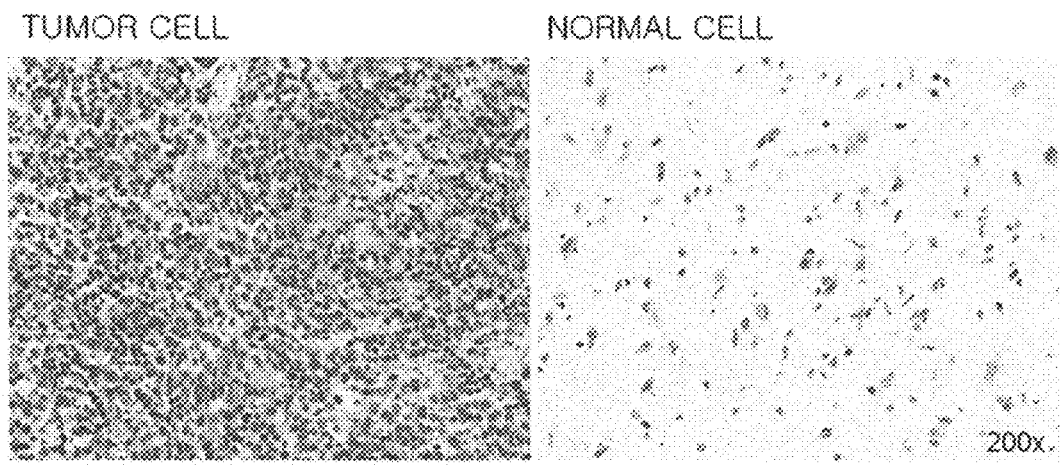
FIGS. 3A through 3C present images showing results of performing an immunohistochemistry staining reaction of c-Met in normal cells and tumor cells using monoclonal antibody AbF24 (FIG. 3A), monoclonal antibody Stan34 (FIG. 3B), and a commercially available anti-c-Met antibody (Zymed.
Figure 3B:
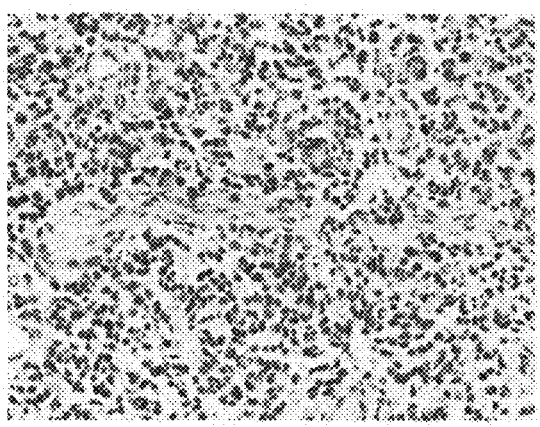
Figure 3B:
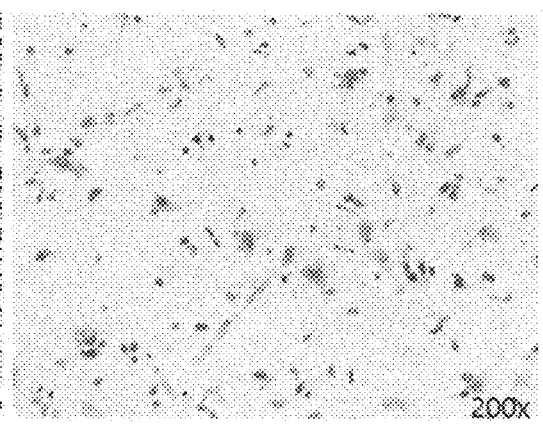
Figure 3C:
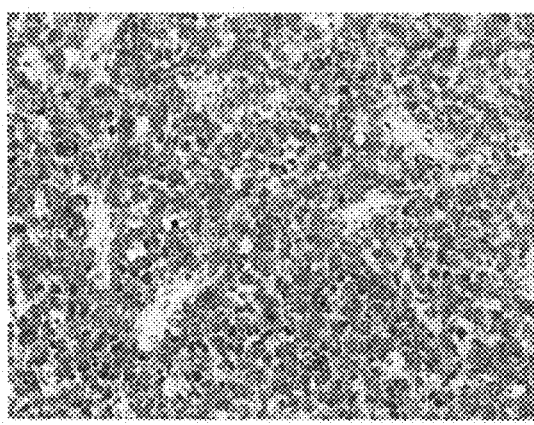
Figure 3C:
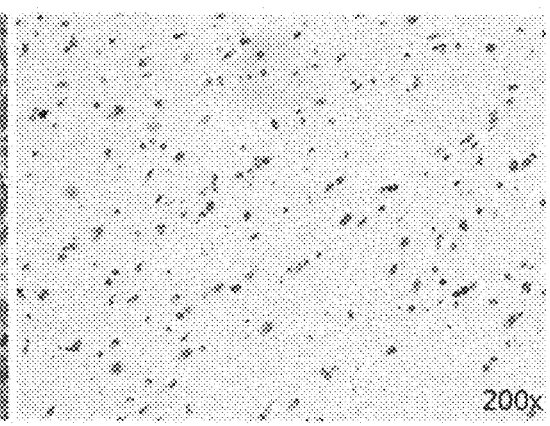

Referring to FIGS. 3A and 3B, expression of c-Met was higher in the tumor cells than the normal cells based on the increased amount of immunohistochemical staining using AbF24 or Stan34 seen in the tumor cells compared to the normal cells. Additionally the images show that monoclonal antibody AbF24 recognized c-Met existing in the cell cytoplasm, while monoclonal antibody Stan34 recognized c-Met existing in the cell nucleus. FIG. 3C shows results of performing an immunohistochemistry staining reaction in normal cells and tumor cells using the commercially available mouse anti-c-MET monoclonal antibody, which is specific for the cytoplasmic domain of c-Met protein. Referring to FIG. 3C, the cells stained by the commercially available mouse anti-c-MET monoclonal antibody are cells in which c-Met was over-expressed, corroborating the results obtained by staining of the monoclonal antibodies AbF24 and Stan34.

Example 6

Immunohistochemistry Staining Reaction of c-Met in HEK293 Cell Line in which Expression Amount of c-Met is Increased, Using Monoclonal Antibodies AbF24 and Stan34

Figure 4:
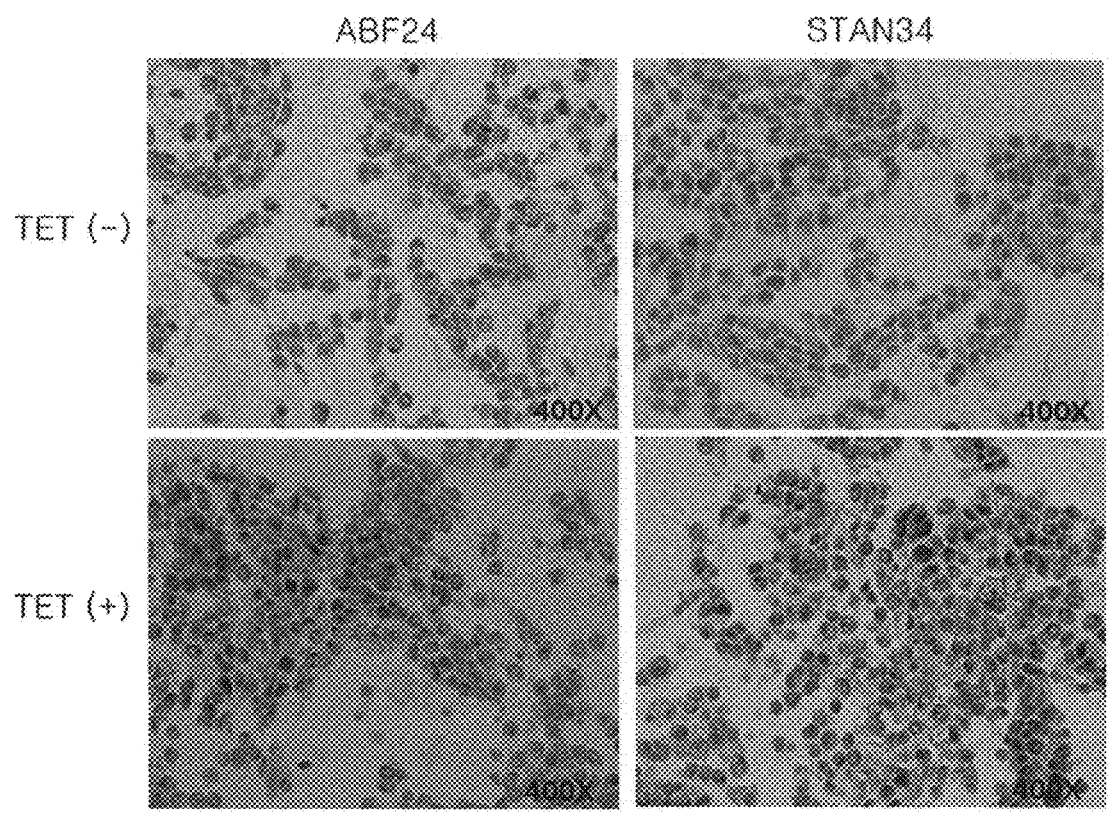
FIG. 4 presents images showing results of performing an immunohistochemistry staining of HEK293 cells with tetracycline (TET)-regulated expression of c-Met, using monoclonal antibodies AbF24 or Stan34, according to an embodiment of the invention.

A HEK293 cell line with tetracycline-regulated expression of c-Met was cultured in the presence or absence of tetracycline as described in Example 4. Cells were collected, and then immunohistochemistry staining was performed on by the methods described in Example 5 using the monoclonal antibodies AbF24 and Stan34 as the primary antibodies and counterstaining with Mayer's hematoxylin. FIG. 4 shows images of stained cells grown in the absence (−) or presence (+) of tetracycline.

In the HEK293 cell line treated with tetracycline the expression level of c-Met was increased over the endogenous expression in the absence of tetracycline. FIG. 4 shows that the number of cells stained by each of the monoclonal antibodies AbF24 and Stan34 increased in the tetracycline-treated cells, corresponding to the increased expression of c-Met in the cells. In addition, as observed in Example 5, the monoclonal antibody AbF24 recognized c-Met protein mainly in cytoplasm, while the monoclonal antibody Stan34 recognized c-Met proteins mainly in the nucleus.

Example 7

CDR Amino Acid Sequences of Monoclonal Antibodies AbF24 and Stan34

The heavy and light chain CDR amino acid sequences of the monoclonal antibodies AbF24 and Stan34 were determined and are shown in Table 4 below. These CDR amino acid sequences in Table 4 were determined to be different from CDR amino acid sequences of other known antibodies recognizing c-Met.

TABLE 4

|  | CDR1 | CDR2 | CDR3 |
|---|---|---|---|
| AbF24 heavy chain | DYSMH (SEQ ID NO: 1) | WINTETGAPTY ADDFKG (SEQ ID NO: 2) | ASMISFVYW GQGTLV (SEQ ID NO: 3) |
| AbF24 light chain | KSSQSLLYSSN QKNYLA (SEQ ID NO: 5) | WASTRKS (SEQ ID NO: 6) | DYPFTFGS GTK (SEQ ID NO: 7) |
| Stan34 heavy chain | DYYMH (SEQ ID NO: 9) | DINPNYGSTKY NQKFQG (SEQ ID NO: 10) | DGQHAMDFW GQGIS (SEQ ID NO: 11) |
| Stan34 light chain | KSSQSLFNSGH QKNYLA (SEQ ID NO: 13) | GASTRES (SEQ ID NO: 14) | LTFGAGTK (SEQ ID NO: 15) |

As described above, provided herein are antibodies specifically binding to c-Met protein and a kit for detecting cancer comprising the antibodies, whereby cancer may be efficiently detected in a sample by confirming whether or not c-Met protein is over-expressed by the sample.

The terminology used herein is for the purpose of describing particular embodiments only and is not intended to be limiting of the invention. The terms "a" and "an" do not denote a limitation of quantity, but rather denote the presence of at least one of the referenced item. The terms "comprising", "having", "including", and "containing" are to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. No language in the specification should be construed as indicating any non-claimed element as essential to the practice of the invention as used herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A monoclonal antibody produced from a hybridoma cell having accession number KCLRF-BP-00219 or accession number of KCLRF-BP-00223, and specifically binding to c-Met protein, or an antigen binding fragment of the monoclonal antibody.

2. The monoclonal antibody of claim 1, comprising an IgG1-type antibody.

3. The monoclonal antibody of claim 1, wherein the c-Met protein is derived from a human or mouse.

4. An isolated antibody that specifically binds to c-Met protein or an antigen binding fragment thereof, the antibody or the antigen binding fragment thereof comprising
   a heavy chain variable region comprising heavy chain complementarity determining region (CDR) amino acid sequences SEQ ID NO: 1, SEQ ID NO: 2, and SEQ ID NO: 3; and
   a light chain variable region comprising light chain CDR amino acid sequences SEQ ID NO: 5, SEQ ID NO: 6, and SEQ ID NO: 7.

5. The antibody or antigen binding fragment thereof of claim 4, wherein the heavy chain variable region comprises an amino acid sequence of SEQ ID NO: 4, and the light chain variable region comprises an amino acid sequence of SEQ ID NO: 8.

6. An antibody that specifically binds to c-Met protein or an antigen binding fragment thereof, the antibody or the antigen binding fragment thereof comprising
   a heavy chain variable region comprising heavy chain complementarity determining region (CDR) amino acid sequences SEQ ID NO: 9, SEQ ID NO: 10, and SEQ ID NO: 11; and
   a light chain variable region comprising light chain CDR amino acid sequences SEQ ID NO: 13, SEQ ID NO: 14, and SEQ ID NO: 15.

7. The antibody or antigen binding fragment thereof of claim 6, wherein the heavy chain variable region comprises an amino acid sequence of SEQ ID NO: 12, and the light chain variable region comprises an amino acid sequence of SEQ ID NO: 16.

8. A hybridoma cell having Accession Number: KCLRF-BP-00219.

9. A hybridoma cell having Accession Number: KCLRF-BP-00223.

10. A method of detecting c-Met protein, the method comprising
    contacting a sample isolated from a subject with the antibody or antigen binding antibody fragment of claim 1; and
    detecting antibody bound to c-Met protein.

11. A method of detecting c-Met protein, the method comprising
    contacting a sample isolated from a subject with the antibody or antigen binding antibody fragment of claim 4; and
    detecting antibody bound to c-Met protein.

12. A method of detecting c-Met protein, the method comprising
    contacting a sample isolated from a subject with the antibody or antigen binding antibody fragment of claim 6; and
    detecting antibody bound to c-Met protein.

13. A composition comprising the isolated antibody or the antigen binding antibody fragment of claim 1; and a pharmaceutically acceptable excipient.

14. A composition comprising the isolated antibody or the antigen binding antibody fragment of claim 4; and a pharmaceutically acceptable excipient.

15. A composition comprising the isolated antibody or the antigen binding antibody fragment of claim 6; and a pharmaceutically acceptable excipient.

16. A polynucleotide encoding the antibody of claim 4.
17. A polynucleotide encoding the antibody of claim 5.
18. A polynucleotide encoding the antibody of claim 6.
19. A polynucleotide encoding the antibody of claim 7.
20. A vector comprising the polynucleotide of claim 16.
21. A vector comprising the polynucleotide of claim 17.
22. A vector comprising the polynucleotide of claim 18.
23. A vector comprising the polynucleotide of claim 19.
24. A host cell comprising the vector of claim 20.
25. A host cell comprising the vector of claim 21.
26. A host cell comprising the vector of claim 22.
27. A host cell comprising the vector of claim 23.

* * * * *

```
                        SEQUENCE LISTING

<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: heavy chain CDR1 of monoclonal antibody AbF24

<400> SEQUENCE: 1

Asp Tyr Ser Met His
 1               5

<210> SEQ ID NO 2
<211> LENGTH: 17
<212> TYPE: PRT
<213> ORGANISM: Artificial Sequence
<220> FEATURE:
<223> OTHER INFORMATION: heavy chain CDR2 of monoclonal antibody AbF24

<400> SEQUENCE: 2

Trp Ile Asn Thr Glu Thr Gly Ala Pro Thr Tyr Ala Asp Asp Phe Lys
 1               5                  10                  15

Gly

<210> SEQ ID NO 3
<211> LENGTH: 15
<212> TYPE: PRT
<213> ORGANISM: Artificial Sequence
<220> FEATURE:
<223> OTHER INFORMATION: heavy chain CDR3 of monoclonal antibody AbF24

<400> SEQUENCE: 3

Ala Ser Met Ile Ser Phe Val Tyr Trp Gly Gln Gly Thr Leu Val
 1               5                  10                  15

<210> SEQ ID NO 4
<211> LENGTH: 113
<212> TYPE: PRT
<213> ORGANISM: Artificial Sequence
<220> FEATURE:
<223> OTHER INFORMATION: heavy chain variable region of monoclonal
      antibody AbF24
```

<400> SEQUENCE: 4

Gln Ile Gln Leu Val Gln Ser Gly Pro Glu Leu Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Ala Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asp Glu Asp Thr Ala Thr Tyr Phe Cys
                85                  90                  95

Ala Arg Ala Ser Met Ile Ser Phe Val Tyr Trp Gly Gln Gly Thr Leu
            100                 105                 110

Val

<210> SEQ ID NO 5
<211> LENGTH: 17
<212> TYPE: PRT
<213> ORGANISM: Artificial Sequence
<220> FEATURE:
<223> OTHER INFORMATION: light chain CDR1 of monoclonal antibody AbF24

<400> SEQUENCE: 5

Lys Ser Ser Gln Ser Leu Leu Tyr Ser Ser Asn Gln Lys Asn Tyr Leu
1               5                   10                  15

Ala

<210> SEQ ID NO 6
<211> LENGTH: 7
<212> TYPE: PRT
<213> ORGANISM: Artificial Sequence
<220> FEATURE:
<223> OTHER INFORMATION: light chain CDR2 of monoclonal antibody AbF24

<400> SEQUENCE: 6

Trp Ala Ser Thr Arg Lys Ser
1               5

<210> SEQ ID NO 7
<211> LENGTH: 11
<212> TYPE: PRT
<213> ORGANISM: Artificial Sequence
<220> FEATURE:
<223> OTHER INFORMATION: light chain CDR3 of monoclonal antibody AbF24

<400> SEQUENCE: 7

Asp Tyr Pro Phe Thr Phe Gly Ser Gly Thr Lys
1               5                   10

<210> SEQ ID NO 8
<211> LENGTH: 109
<212> TYPE: PRT
<213> ORGANISM: Artificial Sequence
<220> FEATURE:
<223> OTHER INFORMATION: light chain variable region of monoclonal
      antibody AbF24

<400> SEQUENCE: 8

Asp Ile Val Met Ser Gln Ser Pro Ser Ser Leu Ala Val Ser Val Gly
1               5                   10                  15

```
Glu Lys Ile Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Lys Ser Gly Val
        50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                85                  90                  95

Tyr Tyr Asp Tyr Pro Phe Thr Phe Gly Ser Gly Thr Lys
                100                 105

<210> SEQ ID NO 9
<211> LENGTH: 5
<212> TYPE: PRT
<213> ORGANISM: Artificial Sequence
<220> FEATURE:
<223> OTHER INFORMATION: heavy chain CDR1 of monoclonal antibody Stan34

<400> SEQUENCE: 9

Asp Tyr Tyr Met His
 1               5

<210> SEQ ID NO 10
<211> LENGTH: 17
<212> TYPE: PRT
<213> ORGANISM: Artificial Sequence
<220> FEATURE:
<223> OTHER INFORMATION: heavy chain CDR2 of monoclonal antibody Stan34

<400> SEQUENCE: 10

Asp Ile Asn Pro Asn Tyr Gly Ser Thr Lys Tyr Asn Gln Lys Phe Gln
 1               5                  10                  15

Gly

<210> SEQ ID NO 11
<211> LENGTH: 14
<212> TYPE: PRT
<213> ORGANISM: Artificial Sequence
<220> FEATURE:
<223> OTHER INFORMATION: heavy chain CDR3 of monoclonal antibody Stan34

<400> SEQUENCE: 11

Asp Gly Gln His Ala Met Asp Phe Trp Gly Gln Gly Ile Ser
 1               5                  10

<210> SEQ ID NO 12
<211> LENGTH: 112
<212> TYPE: PRT
<213> ORGANISM: Artificial Sequence
<220> FEATURE:
<223> OTHER INFORMATION: heavy chain variable region of monoclonal
      antibody Stan34

<400> SEQUENCE: 12

Glu Val Gln Leu Gln Gln Phe Gly Pro Asp Leu Val Lys Pro Gly Ala
 1               5                  10                  15

Ser Val Arg Ile Ser Cys Lys Ala Ser Gly Tyr Thr Phe Thr Asp Tyr
                20                  25                  30

Asn Met Asp Trp Val Arg Gln Ser His Gly Lys Ser Leu Glu Trp Ile
            35                  40                  45
```

```
Gly Asp Ile Asn Pro Asn Tyr Gly Ser Thr Lys Tyr Asn Gln Lys Phe
        50                  55                  60

Gln Gly Lys Ala Thr Leu Thr Val Asp Glu Ser Ser Asn Thr Ala Tyr
 65                  70                  75                  80

Met Asp Leu Arg Ser Leu Thr Ser Glu Asp Thr Ala Val Tyr Tyr Cys
                 85                  90                  95

Ala Arg Asp Gly Gln His Ala Met Asp Phe Trp Gly Gln Gly Ile Ser
            100                 105                 110

<210> SEQ ID NO 13
<211> LENGTH: 17
<212> TYPE: PRT
<213> ORGANISM: Artificial Sequence
<220> FEATURE:
<223> OTHER INFORMATION: light chain CDR1 of monoclonal antibody Stan34

<400> SEQUENCE: 13

Lys Ser Ser Gln Ser Leu Phe Asn Ser Gly His Gln Lys Asn Tyr Leu
  1               5                  10                  15

Ala

<210> SEQ ID NO 14
<211> LENGTH: 7
<212> TYPE: PRT
<213> ORGANISM: Artificial Sequence
<220> FEATURE:
<223> OTHER INFORMATION: light chain CDR2 of monoclonal antibody Stan34

<400> SEQUENCE: 14

Gly Ala Ser Thr Arg Glu Ser
  1               5

<210> SEQ ID NO 15
<211> LENGTH: 8
<212> TYPE: PRT
<213> ORGANISM: Artificial Sequence
<220> FEATURE:
<223> OTHER INFORMATION: light chain CDR3 of monoclonal antibody Stan34

<400> SEQUENCE: 15

Leu Thr Phe Gly Ala Gly Thr Lys
  1               5

<210> SEQ ID NO 16
<211> LENGTH: 109
<212> TYPE: PRT
<213> ORGANISM: Artificial Sequence
<220> FEATURE:
<223> OTHER INFORMATION: light chain variable region of monoclonal
      antibody Stan34

<400> SEQUENCE: 16

Asp Ile Val Met Thr Gln Ser Pro Ser Ser Leu Ser Val Ser Val Gly
  1               5                  10                  15

Glu Lys Val Ile Met Ser Cys Lys Ser Ser Gln Ser Leu Phe Asn Ser
                 20                  25                  30

Gly His Gln Lys Asn Tyr Leu Ala Trp Tyr Gln Gln Lys Pro Gly Gln
             35                  40                  45

Pro Pro Lys Leu Leu Ile Tyr Gly Ala Ser Thr Arg Glu Ser Gly Val
         50                  55                  60

Pro Asp Arg Phe Thr Gly Ser Gly Ser Gly Thr Glu Phe Thr Leu Thr
 65                  70                  75                  80

Ile Gly Ser Val Gln Ala Glu Asp Leu Ala Val Tyr Tyr Cys Gln Asn
```

```
                85                  90                  95
Asp His Thr Tyr Pro Leu Thr Phe Gly Ala Gly Thr Lys
                100                 105
```

<210> SEQ ID NO 17
<211> LENGTH: 339
<212> TYPE: DNA
<213> ORGANISM: Artificial Sequence
<220> FEATURE:
<223> OTHER INFORMATION: heavy chain variable region of monoclonal
      antibody AbF24

<400> SEQUENCE: 17

```
cagatccagt tggtgcagtc tggacctgag ctgaagaagc ctggagagac agtcaagatc    60
tcctgcaagg cttctggtta taccttcaca gactattcaa tgcactgggt gaagcaggct   120
ccaggaaagg gtttaaagtg gatgggctgg ataaacactg agactggtgc gccaacatat   180
gcagatgact tcaagggacg gtttgccttc tctttggaaa cctctgccag cactgcctat   240
ttgcagatca acaacctcaa agatgaggac acggctacat atttctgtgc tagagcctct   300
atgatctcgt tgtttactg ggccaaggg actctggtc                            339
```

<210> SEQ ID NO 18
<211> LENGTH: 327
<212> TYPE: DNA
<213> ORGANISM: Artificial Sequence
<220> FEATURE:
<223> OTHER INFORMATION: light chain variable region of monoclonal
      antibody AbF24

<400> SEQUENCE: 18

```
gacattgtga tgtcacagtc tccatcctcc ctagctgtgt cagttggaga gaagattact    60
atgagctgca agtccagtca gagccttta tatagtagca tcaaaagaa ctacttggcc    120
tggtaccagc agaaaccagg gcagtctcct aaactgctga tttactgggc atccactagg   180
aaatctgggg tccctgatcg cttcacaggc agtggatctg ggacagattt cactctcacc   240
atcagcagtg tgaaggctga agacctggca gtttattact gtcagcaata ttatgactat   300
ccattcacgt tcggctcggg gacaaag                                       327
```

<210> SEQ ID NO 19
<211> LENGTH: 336
<212> TYPE: DNA
<213> ORGANISM: Artificial Sequence
<220> FEATURE:
<223> OTHER INFORMATION: heavy chain variable region of monoclonal
      antibody Stan34

<400> SEQUENCE: 19

```
gaggtccagc tgcaacagtt tggacctgac ctggtgaagc ctggggcttc agtgaggata    60
tcctgcaagg cttctggata cacattcact gactacaaca tggactgggt gaggcagagc   120
catggaaaga gccttgagtg gattggagat attaatccga actatggtag tactaagtac   180
aaccagaagt tccaggggaa ggccacattg actgtagacg agtcctccaa cacagcctac   240
atggacctcc gcagcctgac atctgaggac actgcagtct attactgtgc aagagacggt   300
caacatgcta tggacttctg gggtcaagga atctca                             336
```

<210> SEQ ID NO 20
<211> LENGTH: 327
<212> TYPE: DNA
<213> ORGANISM: Artificial Sequence
<220> FEATURE:

-continued

```
<223> OTHER INFORMATION: light chain variable region of monoclonal
      antibody Stan34

<400> SEQUENCE: 20
gacattgtga tgacacagtc tccatcctcc ctgagtgtgt cagtaggaga gaaggtcatt        60
atgagctgca agtccagtca gagtctgttc aacagtggac atcaaaagaa ctacttggcc       120
tggtaccagc agaaaccagg gcagcctcct aaactattga tctacggggc atccactagg       180
gaatctgggg tccctgatcg cttcacaggc agtggatctg gaactgagtt cactcttacc       240
attggcagtg tgcaggctga agacctggca gtttattact gtcagaatga tcatacttat       300
ccgctcacgt tcggtgctgg gaccaag                                           327
```